(12) United States Patent
Petit et al.

(10) Patent No.: US 9,408,383 B2
(45) Date of Patent: Aug. 9, 2016

(54) ROOFING GRANULES

(71) Applicants: Pierre-Olivier Petit, Enghien-les-bains (FR); Keith C. Hong, Lititz, PA (US); Gregory F. Jacobs, Oreland, PA (US); Kamila Plevacova, Courbevoie (FR)

(72) Inventors: Pierre-Olivier Petit, Enghien-les-bains (FR); Keith C. Hong, Lititz, PA (US); Gregory F. Jacobs, Oreland, PA (US); Kamila Plevacova, Courbevoie (FR)

(73) Assignee: CERTAINTEED CORPORATION, Malvern, PA (US)

( * ) Notice: Subject to any disclaimer, the term of this patent is extended or adjusted under 35 U.S.C. 154(b) by 123 days.

(21) Appl. No.: 13/834,722

(22) Filed: Mar. 15, 2013

(65) Prior Publication Data

US 2014/0004168 A1    Jan. 2, 2014

Related U.S. Application Data

(60) Provisional application No. 61/665,410, filed on Jun. 28, 2012.

(51) Int. Cl.
| | | |
|---|---|---|
| *A01N 25/26* | (2006.01) | |
| *A01N 55/00* | (2006.01) | |
| *A01N 25/12* | (2006.01) | |
| *A01N 59/20* | (2006.01) | |

(52) U.S. Cl.
CPC ............... *A01N 25/26* (2013.01); *A01N 25/12* (2013.01); *A01N 55/00* (2013.01); *A01N 59/20* (2013.01)

(58) Field of Classification Search
CPC ....... A01N 25/25; A01N 25/12; A01N 59/20; A01N 55/00; E04D 13/002
See application file for complete search history.

(56) References Cited

U.S. PATENT DOCUMENTS

| | | | |
|---|---|---|---|
| 2,046,295 A | 6/1936 | Nichols | |
| 2,197,895 A | 4/1940 | Nichols | |
| 3,528,842 A | 9/1970 | Skadulis | |
| 5,356,664 A | 10/1994 | Narayan et al. | |
| 5,382,475 A | 1/1995 | Kayser | |
| 5,411,803 A | 5/1995 | George et al. | |
| 6,143,318 A | 11/2000 | Gilchrist et al. | |
| 6,214,466 B1 | 4/2001 | Joedicke | |
| 6,245,381 B1 | 6/2001 | Israel | |
| 6,569,520 B1 | 5/2003 | Jacobs | |
| 6,585,813 B2 | 7/2003 | Kiik et al. | |
| 6,593,260 B2 | 7/2003 | Nomura | |
| 6,815,379 B2 | 11/2004 | Nomura | |
| 6,838,152 B2 | 1/2005 | Joedicke | |
| 6,838,171 B2 | 1/2005 | Nomura | |
| 6,939,820 B2 * | 9/2005 | Numaguchi | C03C 3/16 424/604 |
| 7,060,658 B2 | 6/2006 | Joedicke | |
| 7,323,237 B2 | 1/2008 | Koschitzky | |
| 7,354,596 B1 | 4/2008 | Banovetz et al. | |
| 7,595,107 B2 | 9/2009 | Kalkanoglu et al. | |
| 7,687,106 B2 | 3/2010 | Hong et al. | |
| 7,704,903 B2 | 4/2010 | Seneschal et al. | |
| 7,811,630 B2 | 10/2010 | Hong et al. | |
| 8,039,048 B2 | 10/2011 | Hong et al. | |
| 2001/0023156 A1 | 9/2001 | Nomura | |
| 2002/0098110 A1 | 7/2002 | Graham et al. | |
| 2003/0150170 A1 | 8/2003 | Weber | |
| 2004/0002416 A1 | 1/2004 | Nomura | |
| 2004/0002417 A1 | 1/2004 | Nomura | |
| 2004/0139886 A1 | 7/2004 | Joedicke | |
| 2004/0255548 A1 | 12/2004 | Hong et al. | |
| 2004/0258835 A1 | 12/2004 | Hong et al. | |
| 2005/0031703 A1 | 2/2005 | Beier et al. | |
| 2005/0069592 A1 | 3/2005 | Fechner et al. | |
| 2005/0233888 A1 | 10/2005 | Seneschal et al. | |
| 2006/0142413 A1 * | 6/2006 | Zimmer et al. ................ 523/122 |
| 2006/0166806 A1 | 7/2006 | Fechner et al. | |
| 2006/0172877 A1 | 8/2006 | Fechner et al. | |
| 2006/0251807 A1 | 11/2006 | Hong et al. | |
| 2007/0148340 A1 | 6/2007 | Kalkanoglu et al. | |
| 2007/0148342 A1 | 6/2007 | Kalkanoglu et al. | |
| 2008/0008858 A1 | 1/2008 | Hong et al. | |
| 2008/0026183 A1 | 1/2008 | Vanpoulle et al. | |
| 2008/0118640 A1 | 5/2008 | Kalkanoglu et al. | |
| 2008/0241516 A1 | 10/2008 | Hong et al. | |
| 2008/0248246 A1 | 10/2008 | Shiao et al. | |
| 2008/0261007 A1 | 10/2008 | Hong et al. | |
| 2008/0277056 A1 * | 11/2008 | Kalkanoglu et al. .......... 156/280 |
| 2010/0098777 A1 | 4/2010 | Gould et al. | |
| 2010/0240526 A1 | 9/2010 | Hong et al. | |
| 2011/0159237 A1 | 6/2011 | Bryson et al. | |
| 2011/0159240 A1 | 6/2011 | Shiao et al. | |
| 2012/0157583 A1 | 6/2012 | Shiao et al. | |

FOREIGN PATENT DOCUMENTS

| | | | |
|---|---|---|---|
| CA | 2041964 | A1 | 11/1991 |
| DE | 4130365 | A1 | 3/1993 |
| DE | 19943303 | A1 | 3/2001 |
| DE | 10300813 | A1 | 7/2004 |
| DE | 10308186 | A1 | 9/2004 |
| EP | 0458713 | A1 | 11/1991 |
| EP | 1116698 | A1 | 7/2001 |
| EP | 1580172 | A2 | 9/2005 |

(Continued)

*Primary Examiner* — Frederick Krass
*Assistant Examiner* — Tracy Liu
(74) *Attorney, Agent, or Firm* — Abel Law Group, LLP; Alexander H. Plache (57) ABSTRACT

A biocidal glass composition for use in roofing applications can include glass doped with at least one biocidal agent that includes about 0.01 wt. % to about 50 wt. % of a total weight % of the biocidal glass composition. The biocidal glass composition can be included in a coating on a base particle of a roofing granule. Further included is a process of forming the roofing granule.

15 Claims, 5 Drawing Sheets

(56) References Cited

FOREIGN PATENT DOCUMENTS

| | | |
|---|---|---|
| FR | 2866371 A1 | 8/2005 |
| WO | 9419415 A1 | 9/1994 |
| WO | 9624364 A2 | 8/1996 |
| WO | 9956542 A1 | 11/1999 |
| WO | 0108494 A1 | 2/2001 |
| WO | 0204762 A1 | 1/2002 |
| WO | 03062163 A2 | 7/2003 |
| WO | 2004076370 A1 | 9/2004 |
| WO | 2004076371 A2 | 9/2004 |
| WO | 2008045992 A1 | 4/2008 |
| WO | 2012135194 A1 | 10/2012 |
| WO | WO 2012135194 A1 * 10/2012 | ............. C03C 3/089 |

* cited by examiner

ROOFING GRANULES

FIELD OF THE DISCLOSURE

The present disclosure relates to roofing granules and processes of forming the roofing granules and, more particularly, to roofing granules including biocidal glass compositions and to processes of forming the roofing granules with the biocidal glass compositions.

BACKGROUND

Roofing materials are susceptible to infestation of various microorganisms, including fungi, bacteria and blue-green algae, which result in undesirable dark streaks on roofing surfaces after only a few years in service. Previous solutions that rely on applications of organic or inorganic biocides, metal strips, or metal oxides to inhibit or delay the microorganism infestation are only effective for a few years, usually less than ten years.

Accordingly, there is a need for an improved biocidal roofing material.

SUMMARY

In an embodiment, a biocidal glass composition for use in roofing applications is provided wherein the biocidal glass composition includes glass doped with at least one biocidal agent and wherein the at least one biocidal agent includes about 0.01 wt. % to about 50 wt. % of a total weight % of the biocidal glass composition.

In another embodiment, a roofing granule is provided wherein the roofing granule includes a base particle and a coating formed along a surface of the base particle, wherein the coating includes a biocidal glass composition including glass doped with at least one biocidal agent, and wherein the at least one biocidal agent includes about 0.01 wt. % to about 50 wt. % of a total weight % of the biocidal glass composition.

In yet another embodiment, a process of forming a roofing granule includes providing a base particle and forming a first coating along a surface of the base particle, wherein the coating includes a biocidal glass composition, wherein the biocidal glass composition includes a glass doped with at least one biocidal agent, and wherein the at least one biocidal agent includes about 0.01 wt. % to about 50 wt. % of a total weight % of the biocidal glass composition.

In an embodiment, a biocidal glass composition for use in roofing applications is provided. The biocidal glass composition includes silicon dioxide in an amount of about 20 wt. % to about 60 wt. %, boron trioxide in an amount of about 0.1 wt. % to about 20.0 wt. %, and aluminum oxide in an amount of about 0.01 wt. % to about 12.0 wt. %, based on the total weight % of the biocidal glass composition. The biocidal glass is doped with at least one biocidal agent comprising about 0.01 wt. % to about 50 wt. % of a total weight % of the biocidal glass composition.

In still yet another embodiment, a roofing granule includes a base particle and a coating formed along a surface of the base particle. The coating includes a biocidal glass composition having silicon dioxide in an amount of about 20 wt. % to about 60 wt. %, boron trioxide in an amount of about 0.1 wt. % to about 20.0 wt. %, and aluminum oxide in an amount of about 0.01 wt. % to about 12.0 wt. %, based on the total weight % of the biocidal glass composition. The biocidal glass is doped with at least one biocidal agent including about 0.01 wt. % to about 50 wt. % of a total weight % of the biocidal glass composition.

BRIEF DESCRIPTION OF THE DRAWINGS

Embodiments are illustrated by way of example and are not limited in the accompanying figures.

Skilled artisans appreciate that elements in the figures are illustrated for simplicity and clarity and have not necessarily been drawn to scale. For example, the dimensions of some of the elements in the figures may be exaggerated relative to other elements to help to improve demonstration of embodiments of the invention.

DETAILED DESCRIPTION

The following description in combination with the figures is provided to assist in demonstrating the teachings disclosed herein. The following discussion will focus on specific implementations and embodiments of the teachings. This focus is provided to assist in describing the teachings and should not be interpreted as a limitation on the scope or applicability of the teachings. However, other teachings can certainly be used in this application.

Before addressing details of the embodiments described below, some terms are defined or clarified. The term "averaged" is intended to mean an average (i.e., an arithmetic mean), a median, or a geometric mean.

In this specification, color may be expressed as a color space that is specified by a set of 1976 CIE (Commission Internationale de L'Eclairage) color space coordinates of L*, a*, and b*, wherein L* represents lightness of the color (L*=0 is black, and L*=100 indicates diffuse white; specular white may be higher), a* represents a position between red/magenta and green (a* negative values indicate green while positive values indicate magenta), and b* represents a position between yellow and blue (b* negative values indicate blue and positive values indicate yellow).

As used herein, the terms "comprises," "comprising," "includes," "including," "has," "having" or any other variation thereof, are intended to cover a non-exclusive inclusion. For example, a method, article, or apparatus that comprises a list of features is not necessarily limited only to those features but may include other features not expressly listed or inherent to such method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" is employed to describe elements and components described herein. This is done merely for convenience and to give a general sense of the scope of the invention. This description should be read to include one or at least one and the singular also includes the plural, or vice versa, unless it is clear that it is meant otherwise. For example, when a single item is described herein, more than one item may be used in place of a single item. Similarly, where more than one item is described herein, a single item may be substituted for that more than one item.

Unless otherwise defined, all technical and scientific terms used herein have the same meaning as commonly understood by one of ordinary skill in the art to which this invention belongs. The materials, methods, and examples are illustrative only and not intended to be limiting. To the extent not described herein, many details regarding specific materials and processing acts are conventional and may be found in reference books and other sources within the structural arts and corresponding manufacturing arts.

The present invention provides a biocidal glass composition for use in roofing applications. The biocidal glass composition includes glass doped with at least one biocidal agent, where the biocidal agent includes about 0.01 wt. % to about 50 wt. % of a total weight % of the biocidal glass composition. In an embodiment, the biocidal agent can include between about 5 wt. % and about 40 wt. % of the total weight % of the biocidal glass composition, such as between about 20 wt. % and about 35 wt. % of the total weight % of the biocidal glass composition. The term "doped," as used herein, refers to the at least one biocidal agent being at least partly solubilized within the glass composition matrix. "Solubilized" as used herein refers to a biocidal agent that is at least partly dissolved within the glass composition matrix. In conventional roofing granules, the biocidal agent may be encapsulated within or onto a base particle of a roofing granule using an inorganic coating, but the biocidal agent is not solubilized within a glass composition matrix. In the present invention, the biocidal agent is at least partly solubilized within the glass composition matrix to create the biocidal glass composition, which in turn may be applied onto a base particle of a roofing granule using the biocidal glass composition as a coating or as a component of a coating. In an embodiment, the biocidal glass composition of the present invention may also include at least one biocidal agent encapsulated within the glass composition matrix in addition to the at least one biocidal agent that is solubilized within the glass composition matrix. In an exemplary embodiment, the biocidal glass composition of the present invention desirably inhibits or delays microorganism infestation when exposed to an outdoor environment.

The biocidal agent used to dope the biocidal glass composition can include various biocidal agents, including but not limited to the oxidized forms of copper, zinc, silver, tin, or any combination thereof. Any oxidized form of the biocidal agents is envisioned. In embodiment, the biocidal glass composition may include between about 0.1 wt. % and about 50 wt. % of each of zinc oxide, copper oxide, and tin oxide, with the proviso that the total sum of the weight % of each of zinc oxide, copper oxide, and tin oxide is not greater than 100 wt. %. In an embodiment, the biocidal glass composition may further include between about 0.01 wt. % and about 2 wt. % of silver oxide. In an exemplary embodiment, the biocidal agent includes copper oxide, such as CuO and $Cu_2O$. In an embodiment, the copper oxide is present at an amount of about 0.1 wt. % to about 50 wt. % based on the total amount of the biocidal glass composition.

In an embodiment, the biocidal glass composition can include more than one biocidal agent. Any combination of biocidal agents may be envisioned. For example, the biocidal glass composition can include between about 1 wt. % and about 10 wt. % of zinc oxide and between about 10 wt. % and 30 wt. % of copper oxide. The biocidal agent can also be incorporated into the biocidal glass composition in more than one manner. For example, the biocidal glass composition may be doped with a portion of the biocidal agent (e.g., where the biocidal agent is a soluble portion of the biocidal glass composition) and may also encase or encapsulate another portion of the biocidal agent as an inclusion.

The biocidal glass composition can include any reasonable glass composition. The glass composition provides the matrix in which the biocidal agent is at least partly solubilized. In an embodiment, the biocidal glass composition includes a glass composition including, but not limited to, soda-lime silicate glass, float glass, phosphate glass, borate glass, the like, or any combination thereof. In an embodiment, such a glass composition includes soda-lime silicate glass, and in particular, the glass composition can include silicon dioxide. In a particular embodiment, the biocidal glass composition can include about 20 wt. % to about 60 wt. % of silicon dioxide, based on the total weight % of the biocidal glass composition. The various compositions of glass can be obtained through a variety of sources, including through a dedicated production process or by recycling waste glass from the glass industry or from domestic sources.

In addition to the glass composition being doped with one or more biocidal agents, the glass composition may include a variety of other compounds. In a particular embodiment, the glass composition may include an oxidized formed of aluminum, boron, calcium, magnesium, sodium, potassium, or any combination thereof. Any reasonable amount of the compounds is envisioned. For instance, certain oxidized compounds may be used to provide desirable properties to the final biocidal glass composition, such as stability, durability, controlled leaching of the biocidal agent, or any combination thereof. In particular, the compounds of the glass composition may be optimized depending on the final properties desired for the coated roofing granule.

In an embodiment, the glass composition includes oxides of boron. In a particular embodiment, the oxide of boron includes boron trioxide. The boron trioxide provides desirable properties to the final biocidal glass composition, such as, for example, improved leaching properties of the biocidal agent such that a controlled release of the biocidal agent can be obtained compared to a biocidal glass composition without boron trioxide. In a particular embodiment, the boron trioxide provides a higher limit of leachable biocidal agent over an extended period of time compared to a biocidal glass composition without boron trioxide. Advantageously, the increased leaching properties of the biocidal agent due to the presence of boron trioxide in the glass composition can provide a desirable biocidal effect wherein less glass may be used on the roofing granules compared to a biocidal glass composition without boron trioxide. In a further embodiment, the presence of the boron trioxide increases the useful active lifetime of the glass when the biocidal glass composition is exposed to an acidic environment. "An acidic environment" as used herein refers to an aqueous environment having a pH of less than 7, such an aqueous environment at a pH of 6, or even a pH of 5 or less. The boron trioxide may be present in any reasonable amount to improve the properties of the biocidal glass composition. In an exemplary embodiment, boron trioxide may be present at about 0.1 wt. % to about 20.0 wt. %, based on the total weight % of the biocidal glass composition.

In an embodiment, the biocidal glass includes aluminum oxide. The aluminum oxide provides desirable properties to the biocidal glass composition, such as, for example, an improved durability of the biocidal glass composition. In a more particular embodiment, the aluminum oxide provides durable properties to the biocidal glass composition such as stability and a slower dissolution of the biocidal glass composition in an acidic environment compared to a biocidal glass composition without aluminum oxide. In an even more particular embodiment, aluminum oxide may be present in any reasonable amount to increase the durability of the biocidal glass composition when exposed to an acidic environment compared to a biocidal glass composition without the aluminum oxide. For instance, aluminum oxide may be present at about 0.1 wt. % to about 12.0 wt. %, such as about 0.1 wt. % to about 5.0 wt. % based on the total weight % of the biocidal glass composition.

In a particular embodiment, both the boron trioxide and the aluminum oxide are present in the biocidal glass composition to provide a synergistic affect on the final biocidal glass composition. For instance, the boron trioxide and the aluminum oxide are present in combination to provide a controlled release of the biocidal agent. For instance, the dissolution of the biocidal glass composition is slowed when exposed to an acidic environment due to the presence of aluminum oxide and the leachable amount of biocidal agent is maximized due to the present of the boron trioxide. Accordingly, the amount of the boron trioxide and aluminum oxide may be varied and optimized depending on the final properties desired for the final biocidal glass composition.

In an embodiment, the glass composition further includes reasonable amounts of additional compounds. The glass composition may include, for example, oxides of calcium, magnesium, sodium, potassium, or any combination thereof. For example, the final biocidal glass composition may include between about 0 wt. % and about 20 wt. % of each of sodium oxide, potassium oxide, or combination thereof, based on the total weight % of the biocidal composition. The final biocidal glass composition may also include between about 0 wt. % and about 15 wt. % of magnesium oxide, based on the total weight % of the biocidal composition. Further, the final biocidal glass composition may include between about 0 wt. % and about 30 wt. % of calcium oxide, based on the total weight % of the biocidal composition.

The biocidal glass composition can be produced using a variety of techniques. Examples of different compounds being combined to produce different biocidal glass composition samples are shown in Table 2. In an embodiment, the desired compounds that constitute the composition, such as particular weight percentages of one or more biocidal agents and particular weight percentages of one or more glass compounds, are melted together at a high temperature sufficient to produce a homogeneous glass mixture. In an embodiment, the biocidal agents and glass compounds are melted at any reasonable temperature, such as between about 1000° C. and about 1600° C. In a particular embodiment, the biocidal agents and glass compounds are melted at a temperature of at least about 1400° C. to form a molten glass. The molten glass may then be extruded and rolled into flat, engraved sheets to easily break the glass into pieces, such as via crushing, milling, or any combination thereof.

The biocidal glass composition can take various forms, including a powdered form for use in a coating on a base particle of a roofing granule. The powdered form may be achieved using various methods, such as by crushing and milling the biocidal glass composition. The powder can include a plurality of particles, and the particles can include a variety of sizes. Any reasonable size is envisioned. For example, the average grain size distribution (D50) in the powdered form of the biocidal glass composition can be less than about 100 μm, such as within a range between about 5 μm and about 50 μm, or such as less than or equal to 10 μm.

The present invention also provides a roofing granule that includes a base particle and a coating formed along an outside surface of the base particle. In an exemplary embodiment, the coating includes a biocidal glass composition as described above, with glass doped with at least one biocidal agent, where the biocidal agent includes about 0.01 wt. % to about 50 wt. % of a total weight % of the biocidal glass composition. The base particle having the coating can provide a roofing granule that can be either spherical or non-spherical.

The base particles of the present invention can include any reasonable materials. For example, the base particles can include mineral particles of the type typically used for making roofing granules, such as talc, slag, limestone, granite, syenite, diabase, greystone, slate, trap rock, basalt, greenstone, andesite, porphyry, rhyolite, and greystone, or other naturally occurring metamorphic rocks, crushed ceramic particles, sands, gravels, or any particles which are both UV opaque and thermally stable at temperatures greater than about 900° Celsius. In an embodiment, the base particles have a particle size between #6 and #50 U.S. mesh, such as a particle size between #8 and #50 U.S. mesh. Exemplary base particles include roofing base granules with a particle size between #10 and #40 U.S. mesh available from CertainTeed Corporation of Piedmont, Mo., USA. In an embodiment, base particles can include conventional algae-resistant roofing granules available from CertainTeed Corporation. The coating including the biocidal glass composition can be formed along the outside surface of the conventional algae resistant roofing granules to provide another mode of biocidal delivery to a roofing product incorporating the roofing granules. The base particles also include any reasonable dimensions, such as an average diameter of about 0.5 to about 2.0 mm, such as between about 1.0 mm and about 2.0 mm.

In an embodiment, various types of stone dust can also be employed to prepare the base particles. Stone dust is a natural aggregate produced as a by-product of quarrying, stone crushing, machining operations, and similar operations. In yet another embodiment, the base particles of the present invention can also include a ceramic-forming material. For example, the ceramic-forming material includes an aluminosilicate. Any reasonable aluminosilicate, such as a bauxite, may be envisioned. The ceramic-forming material can include uncalcined, partially calcined, or calcined clay. In addition to the at least one aluminosilicate, the ceramic-forming material can include small amounts of other minerals. Any reasonable mineral is envisioned. Other functional additives, such as colorants, algaecides, biocides, or nano-$TiO_2$ can be added to the ceramic-forming material to provide additional functionalities, such as aesthetics, biocidal effects, self-cleaning, and/or nitrogen oxides reduction. Any reasonable functional additive is envisioned depending on the desired properties of the final roofing granule.

The coating formed along the outside surface of the base particle that includes the biocidal glass composition as described above can also include a variety of other compounds, including but not limited to sodium silicate, clay, water, a binder, a sol gel, other additives, or any combination thereof. In addition to alkali metal silicate, a metal phosphate and/or silica can also be used in the coating. Examples of coatings including some of these compounds are described below in Examples 1 and 2. In an embodiment, roofing granules include a coating that includes between about 1 wt. % and about 10 wt. % of sodium silicate, between about 1 wt. % and about 8 wt. % of clay, between about 0.1 wt. % and about 7 wt. % of water, and at least about 0.5 wt. % of biocidal glass composition, with the proviso that each weight % is based upon a total weight % of the total amount of roofing granules. In an embodiment, the coating can include at least about 2 wt. % or even at least about 4 wt. % of the biocidal glass composition. In yet another embodiment, the coating can include any reasonable amount of the biocidal agent and the biocidal agent can be added to any portion of the coating at any point in the process of creating the coating. In a particular embodiment, the coating can include clay doped with any reasonable amount of the biocidal agent. For instance, the doped clay can be combined with sodium silicate using any reasonable method. In an embodiment, the doped clay and sodium silicate are heated to create the coating.

The coating on the base particle may be formed along the outside surface of the base particle in at least one layer. In an embodiment, the coating directly overlies the base particle. When more than one layer is used, the composition of each coating may be the same or different. For example, a first coating can be created using the biocidal glass composition in powdered form along with sodium silicate, clay, water, a binder, a sol gel coating, other additives, or any combination thereof. In a particular embodiment, it is desirable to provide a water content in the first coating. Too little water added to the first coating can create a thick paste that is not processable for coating the base particles. In contrast, too much water added to the first coating can create a paste too thin to adequately and homogeneously coat the base particles in a uniform coating. In an embodiment, the coating may be applied directly to the outer surface of the base particle in layers by a variety of means such that the coating will coat at least about 5% of the outer surface. In an embodiment, the coating will coat at least about 25% of the outer surface, such as greater than 50% or greater than 75%, or up to 100% of the outer surface. The percentage of the outer surface coated with the coating may depend on the method used to coat the base particle. For instance, forming the coating on the base particle includes pan coating, spray coating, fluidized bed coating, dip coating, powder coating, thin film coating, or any combination thereof. In a particular embodiment, the coating may be applied by pan coating. Pan coating includes placing the base particles in a viscous coating and agitating the particles and coating until a continuous coating is formed on the base particles. The coating may be continuous or discontinuous on the surface of the base particles. The term "continuous," as used herein, refers to a coating that includes at least the average thickness of the coating on at least 75% of the outer surface of the base particle. For example, a continuous coating includes at least the average thickness of the coating on at least 85%, such as at least 95%, at least 99%, or up to 100%, of the outer surface of the base particle. The coating may include a variety of layers, each with the same or different biocidal glass compositions included therein.

Once the coating is applied, the coating may be cured by any reasonable means. For instance, the first coating can be applied in a first layer directly onto the outer surface of the base particle and then the first layer of the first coating can be cured by, for example, firing the coated base particle in a kiln. Curing conditions is typically dependent upon the composition of the coating. In an embodiment, the kiln can include a rotary kiln and can include any reasonable firing temperatures, such as a temperature of greater than about 280° C., greater than about 340° C., greater than about 380° C., or greater than about 430° C. or about 500° C. In an embodiment with a sol gel coating binder, the curing temperature can be much lower, such as less than about 350° C., or less than about 300° C., or less than about 260° C., or less than about 230° C., or even less than about 200° C. Once the first layer of coating is cured, a second layer of the first coating, where the second layer has an identical or different composition to the first layer, can be applied to the base particle on top of the first layer and also cured. In an embodiment, the second layer includes a second coating different from the first coating and the second coating can be applied over the first coating. In another embodiment, the first coating can be applied over the second coating. This process of applying layers of coating and curing each layer can be repeated any number of times until the desired weight % of biocidal glass composition, based on the total weight % of the roofing granule, is achieved and the coating achieves a desired thickness. In an embodiment, the roofing granule includes between about 0.1 wt. % to about 30 wt. % of the biocidal glass composition based on the total weight of the roofing granule. For example, the roofing granule includes between about 1 wt. % to about 30 wt. % of the biocidal glass composition, such as between about 2 wt. % and about 15 wt. %. The coating can include a variety of thicknesses, including an average thickness between about 2 µm and about 200 µm. In a particular embodiment, the coating is uniform, wherein the average thickness varies by less than about 20%, such as by less than about 10%, of the total thickness of the coating. In another embodiment, at least a portion of the surface of the base particle is exposed without any coating.

Advantageously, the biocidal glass composition may be varied depending upon the properties desired for the roofing granule. Combinations of various biocidal glass compositions, including compositions utilizing the same or different biocidal agents in the same or different weight percentages, can be used to coat the same roofing granule. For example, combinations of identical or different biocidal glass compositions can be incorporated into different layers of a coating on a base particle of a roofing granule. In an embodiment, different biocidal glass compositions can be separated and incorporated into different coatings on different base particles, and the diverse roofing granules can be included on one roofing product. Granules that incorporate different biocidal glass compositions on the same roofing product can create an algae resistant roofing product with one or more biocidal agents with specific leaching profiles designed and tailored to unique requirements such as the configuration of the roof, the orientation of the roof relative to prevailing wind and light conditions, and the geographical location of the building.

One advantage to including the biocidal glass composition of the present invention in the coating is that the biocidal glass composition is chemically similar to any inorganic binder compounds that may also be used in the coating. The chemical similarity among all of the compounds in the coating may reduce or eliminate any thermal mismatch between the coefficients of thermal expansion of the biocidal glass composition and the inorganic binder compounds. This may also minimize any premature loss of the biocidal agent from the coating during application and curing of the coating layers on the base particles, thereby improving the life and effectiveness of the roofing granules that include the biocidal glass composition.

Another advantage to providing roofing granules with the biocidal glass composition in the coating is that the biocidal agent may leach, or be released from, the roofing granule more slowly than if the biocidal agent were applied in a conventional manner to the base particle, thereby giving the roofing granule a longer functional life. For example, a conventional roofing granule with a biocidal agent applied to the base particle without the benefit of the biocidal glass composition may exhibit a continually decreasing normalized flux of the biocidal agent over time, as the biocidal agent leaches completely from the roofing granule without interruption. By contrast, a roofing granule with a coating that includes the biocidal glass composition exhibits a normalized flux of biocidal agent from the biocidal glass composition that initially decreases and then becomes steady over an extended period of time, such as at least after about 2 years to about 4 years, thereby lengthening the biocidal functionality of the roofing granule. The biocidal glass composition may include more than one biocidal agent, each with its own leaching profile and steady normalized flux value also over an extended period of time. In a particular embodiment, the leaching profile, i.e. rate, of the biocidal glass composition may be controlled depending on the components chosen as the biocidal agent, the glass composition, or combination thereof. For instance, the biocidal glass composition may include optimized levels of copper oxide as the biocidal agent and the glass may include synergistic amounts of boron trioxide and aluminum oxide.

In an embodiment, the biocidal glass composition may include at least a second biocidal agent with a second steady normalized flux from the biocidal glass composition, different than the first steady normalized flux, after about 2 years to about 4 years, which may further enhance the biocidal functionality of the roofing granule. In an embodiment, the normalized flux of at least one biocidal agent may be steady after about 2 years to about 4 years under normal outdoor weather conditions which can depend on the geographical location in which the roofing granule is used. Such weather conditions can vary and can include for example, high temperatures with high levels of humidity in the Southern regions of the United States, high temperatures with lower levels of humidity in the Southwest region of the Unites States, and cooler temperatures with variations in the level of humidity in the Northern regions of the United States.

A further advantage is that roofing granules including the biocidal glass composition in the coating are lighter in color than conventional algae resistant roofing granules that include one or more biocidal agents. Achieving a lighter-colored granule, such as a buff or cream colored granule, advantageously allows for a broader color palette for roofing products that has not been available previously for conventional algae resistant granules. For example, the coated granule of the present invention can include an L* value of at least 40, as measured by a CIE LAB color scale. In an embodiment, the coated granule can include an L* value of at least 45, such as at least 50, or at least 57, or at least 62, as measured by the CIE LAB color scale. Such lighter-colored algae resistant granules improve solar reflective roofing by preventing biosoiling of the roofing product and maintaining the reflectivity efficiency of the roofing product after an extended period of service. Yet another advantage to providing roofing granules with the biocidal glass composition in the coating is that, in certain embodiments, less biocidal agent is needed to obtain the same level of biocidal functionality as is observed in conventional roofing granules, making the roofing granules of the present invention more efficient. In an embodiment, less glass may be used when the biocidal agent is combined with a glass composition compound that increases the leaching of the biocidal agent.

A roofing product, such as an asphalt-based shingle, can include a total amount of roofing granules, where various percentages of that total amount of roofing granules can be roofing granules loaded with a biocidal glass composition in accordance with the present invention, depending on what biocidal agent(s) is used, the glass composition, and the desired algae resistance. For example, between 0.5% and 100% of the total amount of the roofing granules on the roofing product can include roofing granules loaded with the biocidal glass composition, such as between about 0.5% and about 30%, more than 50%, or as much as up to 100%. The roofing granules of the present invention can also be combined on the roofing product with non-algae resistant granules or conventional algae resistant granules (e.g., granules that include a biocidal agent, but do not include the biocidal glass composition.) The total weight % of the total amount of the roofing granules on the roofing product can also include a variety of weight percentages of one or more biocidal agents. For example, the total amount of roofing granules can include at least 0.1 wt. % of at least one biocidal agent. In an embodiment, the total amount of roofing granules can include at least about 1 wt. %, such as about 3 wt. % or about 5 wt. %, such as about 10 wt. %, or about 20 wt. %, or about 24 wt. %, or about 30 wt. %, or about 35 wt. % of at least one biocidal agent.

Figure 1:
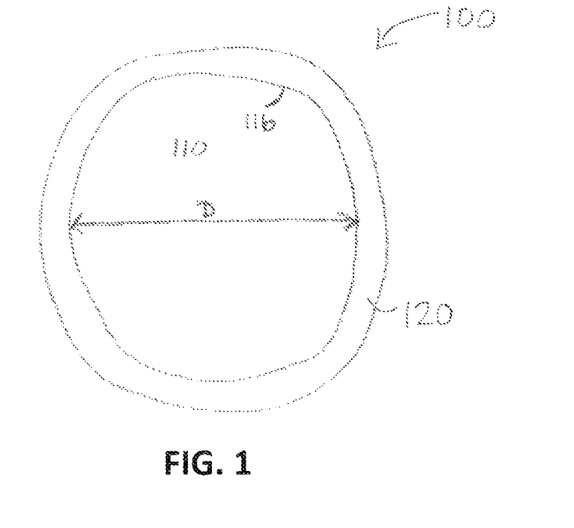
FIG. 1 includes an illustration of a cross-sectional view of a roofing granule in accordance with an embodiment described herein.

Turning to FIG. 1, an illustration of a cross-sectional view of a roofing granule 100 is provided. Granule 100 includes a base particle 110, as described above, with an outer surface 116 that defines an outer diameter D of base particle 110. Granule 100 also includes a coating 120 along the outside surface 116 of base particle 110 and coating 120 may include a variety of thicknesses, including an average thickness of between about 2 μm and about 200 μm. In a particular embodiment, the coating 120 directly contacts the outer surface 116 of base particle 110 without any layers therebetween. Although base particle 110 is shown in FIG. 1 as having a spherical shape with a continuous coating 120, base particle 110 can include various non-spherical configurations and can have any reasonable percentage of its outer surface, such as at least 5%, covered with coating 120. In an embodiment, coating 120 may include a biocidal glass composition with glass doped with at least one biocidal agent, as described above, where the biocidal agent comprises about 0.01 wt. % to about 50 wt. % of a total weight % of the biocidal glass composition. Coating 120 may also include other compounds such as sodium silicate, clay, water, a binder, a sol gel, other additives, or any combination of those compounds in addition to the biocidal glass composition. Coating 120 may be applied in multiple layers onto base particle 110 using a variety of coating methods, such as pan coating, until granule 100 includes a desired weight % of biocidal glass composition. In an embodiment, granule 100 includes about 0.1 wt. % to about 30 wt. % of the biocidal glass composition. Coating 120 also may impart a desired color to granule 100 and in an embodiment, granule 100 with coating 120 has an L* value of at least 40, as measured by a CIE LAB color scale. Granule 100 may be included in a roofing product with a variety of other roofing granules that may include similar or different weight percentages of the same or different biocidal glass compositions as in coating 120 or that may include conventional roofing granules without the biocidal glass composition. In an embodiment, the roofing product includes a total amount of roofing granules, and the total weight % of that total amount of roofing granules includes at least about 0.1 wt. % of the biocidal agent, such as at least about 1 wt. %, or at least about 10 wt. %, or at least about 20 wt. %.

Figure 2:
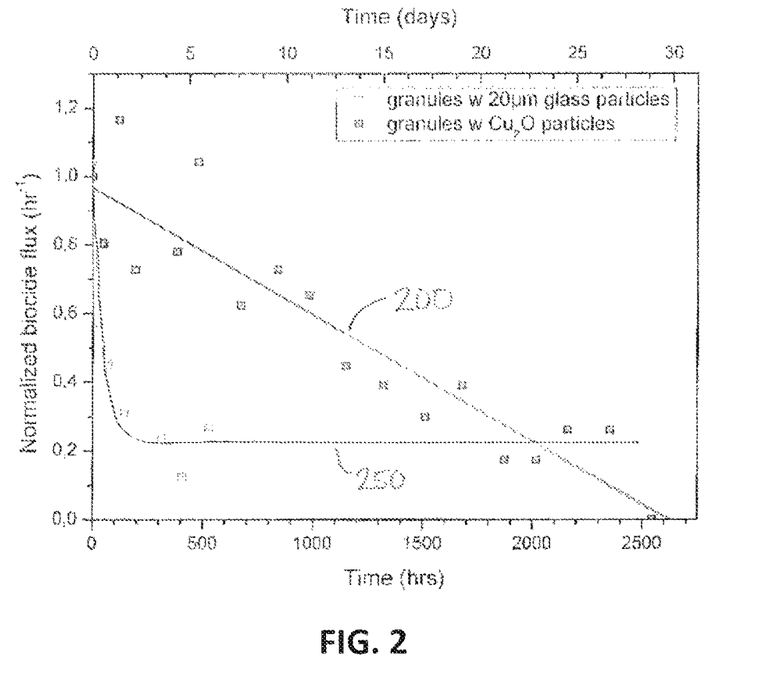
FIG. 2 includes a graph of normalized biocidal agent flux from roofing granules in accordance with an embodiment described herein.

Turning to FIG. 2, a graph of normalized biocidal agent flux from roofing granules is provided. Conventional algae resistant roofing granules that include a biocidal agent, such as copper oxide, without incorporating that biocidal agent in a biocidal glass composition, are provided. Roofing granules in accordance with the present invention and including a coating that includes a biocidal glass composition doped with at least one biocidal agent, such as copper oxide, are also provided. The biocidal glass composition is more fully described as Sample #1 in Example 2 and the biocidal glass composition includes a plurality of particles with an average grain size distribution of about 20 µm. The conventional algae resistant roofing granules and the roofing granules that include a biocidal glass composition in accordance with the present invention are added to a glass container filled with pH 5 buffer solution (based on potassium acid phthalate and sodium hydroxide) at a concentration of 5 g of roofing granules per 500 mL of buffer solution. The containers are immersed in a water bath maintained at a constant temperature of 45° C. The cumulative amount of copper ions that leach out from the roofing granules into the buffer solution and the flux, or rate, of that leaching are measured following the colorimetric bicinchoninate method of the Hach Company (Product No. 2105869). The flux measurements obtained from the test are normalized to provide a normalized biocidal agent flux from the roofing granules.

The normalized flux of the biocidal agent from the conventional algae resistant roofing granules is shown by line 200. Line 200 indicates that the normalized flux decreases steadily over time until it reaches a zero value after approximately 30 days, when the entire biocidal agent has leached from the conventional algae resistant roofing granules. The roofing granules including the biocidal glass composition in accordance with the present invention also exhibit a leaching of the biocidal agent from the roofing granules over time, the normalized flux of which is shown by curve 250. In contrast with line 200, curve 250 exhibits an initial decrease in the normalized flux of the biocidal agent from the roofing granules, followed by a leveling off period after which the normalized flux of the biocidal agent achieves a steady value in which an approximately steady amount of biocidal agent leaches from the roofing granules of the present invention. At approximately 22 to 23 days, curve 250 and line 200 intersect, after which curve 250 retains its normalized flux value while line 200 continues decreasing toward a zero value, indicating that the roofing granules of the present invention retain their biocidal functionality over a longer time period than the conventional algae resistant roofing granules.

The following examples and tables are provided to better disclose and teach processes and compositions of the present invention. They are for illustrative purposes only, and it must be acknowledged that minor variations and changes can be made without materially affecting the spirit and scope of the invention as recited in the claims that follow.

EXAMPLES AND TABLES

TABLE 1

| Compound | Minimum Weight % | Maximum Weight % |
|---|---|---|
| Silicon Dioxide | 20 | 60 |
| Aluminum Oxide | 0.1 | 12 |

TABLE 1-continued

| Compound | Minimum Weight % | Maximum Weight % |
|---|---|---|
| Calcium Oxide | 0 | 30 |
| Magnesium Oxide | 0 | 15 |
| Sodium Oxide | 0 | 20 |
| Potassium Oxide | 0 | 20 |
| Boron Trioxide | 0.1 | 20 |
| Zinc Oxide | 0.1 | 50 |
| Copper Oxide | 0.1 | 50 |
| Silver Oxide | 0.01 | 2 |
| Tin Oxide | 0.1 | 50 |

Table 1 lists exemplary compounds and their ranges of weight percentages in a biocidal glass composition according to the present invention. The first seven compounds may represent the possible compounds used in the glass portion and the bottom four compounds may represent the possible biocidal agents. The biocidal glass composition may be formed in a variety of ways, including for example, by melting all of the desired compounds at a high temperature (e.g., between about 1000° C. and about 1600° C.) to obtain a homogeneous glass mixture.

TABLE 2

| Sample | $SiO_2$ | $Al_2O_3$ | CaO | MgO | $Na_2O$ | $K_2O$ | $B_2O_3$ | ZnO | CuO |
|---|---|---|---|---|---|---|---|---|---|
| 1 | 53 | 4 | 3 | 0 | 11 | 3 | 11 | 5 | 10 |
| 2 | 43 | 0 | 7 | 0 | 14 | 0 | 11 | 5 | 20 |
| 3 | 50.3 | 0 | 8.3 | 3.8 | 12.8 | 0 | 0 | 5 | 20 |
| 4 | 43 | 0 | 3 | 0 | 14 | 0 | 5 | 5 | 30 |
| 5 | 43.6 | 0 | 7.2 | 3.3 | 11.1 | 0 | 0 | 5 | 30 |
| 6 | 53 | 0 | 13 | 0 | 9 | 0 | 0 | 5 | 20 |
| 7 | 43 | 0 | 18 | 0 | 14 | 0 | 0 | 5 | 20 |
| 8 | 33 | 0 | 23 | 0 | 19 | 0 | 0 | 5 | 20 |
| 9 | 33 | 10 | 18 | 0 | 14 | 0 | 0 | 5 | 20 |
| 10 | 43 | 0 | 9.5 | 0 | 14 | 0 | 11 | 2.5 | 20 |
| 11 | 43 | 0 | 12 | 0 | 14 | 0 | 11 | 0 | 20 |
| 12 | 43 | 0 | 13 | 0 | 14 | 0 | 5 | 5 | 20 |
| 13 | 33 | 10 | 7 | 0 | 14 | 0 | 11 | 5 | 20 |
| 14 | 38 | 5 | 7 | 0 | 14 | 0 | 11 | 5 | 20 |
| 15 | 42 | 1 | 12 | 0 | 14 | 0 | 11 | 0 | 20 |
| 16 | 41 | 2 | 12 | 0 | 14 | 0 | 11 | 0 | 20 |
| 17 | 41 | 2 | 2 | 0 | 14 | 0 | 11 | 0 | 30 |

Table 2 lists seventeen different samples of biocidal glass compositions prepared in accordance with the present invention. For each sample, the weight percentage of each compound, based on the total weight percentage of the biocidal glass composition, is provided. The biocidal glass composition includes zinc oxide, copper oxide, or a combination thereof as biocidal agents. Sample #1 is used in association with the normalized biocide flux discussion of FIG. 2.

Example 1

Figure 3:
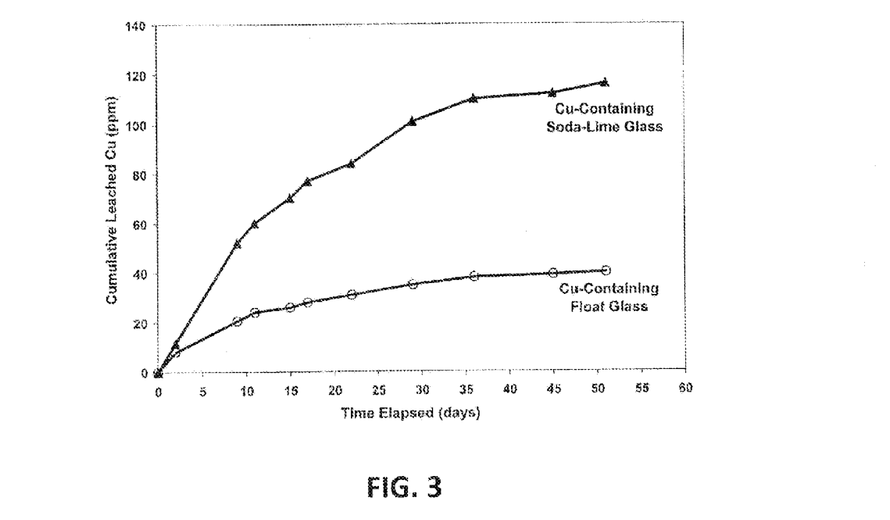
FIG. 3 includes a graph of cumulative biocidal agent ions leached from two biocidal glass compositions over time in accordance with an embodiment described herein.

A biocidal glass composition based on soda-lime glass includes silicon oxide (48 wt. %, based on the total weight % of the biocidal glass composition), sodium oxide (10 wt. %), boron trioxide (11 wt. %), copper oxide (20 wt. %) and zinc oxide (5 wt. %) is melted at 1400° C. to form a homogeneous glass mixture. The biocidal glass composition is cooled, crushed and milled into a powder including a plurality of particles, with an average particle size of 10 µm (D50 value). The biocidal glass composition is formulated in a coating mixture with sodium silicate, clay, and water as the first layer on base particles in the preparation of algae resistant roofing granules. The prepared roofing granules include, by total weight: crushed rock (500 g) for the base particles, sodium silicate (22 g), clay (12 g), water (5 g), and the biocidal glass composition (24 g). The coated roofing granules are fired in a rotary kiln at 450° C. for 20 minutes. After the roofing granules are cooled down to room temperature, a second identical layer of the coating mixture with the biocidal glass composition is applied to the roofing granules and the roofing granules are also fired in the rotary kiln at 450° C. for 20 minutes. The final roofing granules include 4.5 wt. % of the biocidal glass composition, based on a total weight % of the total amount of roofing granules. The cumulative amount of copper ions that leach from these roofing granules containing this first biocidal glass composition over time is shown in FIG. 3.

Example 2

A biocidal glass composition based on float glass includes silicon oxide (50 wt. %, based on the total weight % of the biocidal glass composition), sodium oxide (13 wt. %), calcium oxide (8 wt. %), copper oxide (20 wt. %) and zinc oxide (5 wt. %) is melted at 1400° C. to form a homogeneous glass mixture. Using an identical formulation and preparation procedure as described in Example 1 above, roofing granules are prepared using this biocidal glass composition. The cumulative amount of copper ions that leach from these roofing granules containing this second biocidal glass composition over time is also shown in FIG. 3.

The roofing granules from Examples 1 and 2 are added to a glass container filled with pH 5 buffer solution (based on potassium acid phthalate and sodium hydroxide) at a concentration of 5 g of roofing granules per 500 mL of buffer solution. The containers are immersed in a water bath maintained at a constant temperature of 45° C. The cumulative amount of copper ions that leach out from the roofing granules into the buffer solution is measured following the colorimetric bicinchoninate method of the Hach Company (Product No. 2105869).

Turning to FIG. 3, a graph of cumulative copper ions leached from roofing granules including the two different biocidal glass compositions of Examples 1 and 2 over time is provided. The cumulative leached copper ion amount is plotted as a function of time elapsed in days. These data demonstrate that while the initial biocidal agent weight % are the same in each biocidal glass composition (20 wt. % of copper oxide), variations in the composition of the glass component can result in different solubility and leachability profiles for the biocidal agent from the roofing granules. Both glass variations, however, also exhibit a decreasing rate of leachability over time which permits the roofing granules to retain a desirable biocidal function over a longer period of time.

Example 3

A color measurement test, using Hunter LabScan equipment, is performed on a roofing granule that includes the biocidal glass composition from Example 1. The roofing granule includes 1.9 wt. % of copper oxide, as determined by X-ray fluorescence. The results are compared to the color measurement test results obtained from a conventional algae resistant granule that includes 1 wt. % of copper oxide, but without the biocidal glass composition of the present invention. The results are summarized in Table 3.

TABLE 3

| Granule | L* | a* | b* |
| --- | --- | --- | --- |
| Conventional roofing granule (1 wt. % copper oxide) | 35.48 | 2.08 | 4.50 |
| Roofing granule with biocidal glass composition from Example 1 (1.9 wt. % copper oxide) | 45.64 | 7.21 | 27.97 |

Normally, an increasing amount of copper oxide in a roofing granule results in a darker roofing granule, which may not be desirable in all applications. Table 3 demonstrates, however, that although the roofing granule of the present invention includes nearly twice the weight % of copper oxide as compared to the conventional roofing granule, it also has a higher L* value, indicating a lighter color. The roofing granule of the present invention is lighter in color because applying a coating including the biocidal glass composition to the base particle results in a lighter-colored roofing granule than if a formulation of pure copper oxide is applied to a base particle. The higher b* value of the roofing granule of the present invention also indicates that this roofing granule has a more yellowish tone. The lighter color permits a wider range of desirable color palettes for roofing applications, such as beige.

Example 4

Four different roofing shingles including roofing granules are prepared and compared to examine their percentage of algae infestation over time. The preparations are summarized in Table 4.

TABLE 4

| Shingle | Cu-carrier | D50 (μm) | Copper Oxide (wt. % of granule) | % AR of granules | Average Copper Oxide (total wt. % of granules on shingle) |
| --- | --- | --- | --- | --- | --- |
| 1 | None | None | 0 | None | 0 |
| 2 | Copper Oxide | 10 | 3 | 8 | 0.24 |
| 3 | Biocidal Glass Composition with 10 wt. % Copper Oxide | 10 | 0.3 | 100 | 0.3 |
| 4 | Biocidal Glass Composition with 10 wt. % Copper Oxide | 5 | 0.3 | 100 | 0.3 |

Shingle 1 is prepared without any copper oxide incorporated into the roofing granules. Shingle 2 is prepared conventionally with copper oxide particles incorporated into the roofing granules, but without the biocidal glass composition of the present invention. Approximately 8% of the roofing granules on Shingle 2 are algae-resistant, as disclosed in the column labeled "% AR of granules." Shingle 3 is prepared according to the present invention, where roofing granules that include base particles have a coating that includes a biocidal glass composition doped with 10 wt. % copper oxide, based on the total weight % of the biocidal glass composition. The average grain size distribution of the biocidal glass composition particles is 10 µm. A roofing granule from Shingle 3 includes 0.3 wt. % of copper oxide and the average weight % of the copper oxide in all of the roofing granules on Shingle 3 is 0.3%, based on the total weight % of the total amount of roofing granules on Shingle 3. Shingle 4 is also prepared like Shingle 3 in accordance with the present invention. Shingle 4 differs from Shingle 3 in that the average grain size distribution of the biocidal glass composition particles in Shingle 4 is 5 µm. A roofing granule from Shingle 4 includes 0.3 wt. % of copper oxide and the average weight % of the copper oxide in all of the roofing granules on Shingle 4 is also 0.3%, based on the total weight % of the total amount of roofing granules on Shingle 4. For both Shingles 3 and 4, 100% of the roofing granules on each shingle is an algae-resistant granule in accordance with the present invention.

Each test specimen (e.g., each shingle) is 5 cm×12.5 cm in size containing an inoculant (1.3 cm×3.8 ncm) at the center. The inoculant is an outdoor exposed shingle that has been fully infested with blue-green algae, which functions as a source of algae for testing. Triplicate samples are tested for each formulation. All test specimens are placed in an environmental chamber with controlled light intensity of 1.5 µW/cm$^2$ (between 290-700 nm), at a temperature of 22-28° C. Each day, the lighting is on between 6:00 AM and 8:00 PM; and test specimens are misted with deionized water for 15 seconds every 30 minutes. For observation of algae growth, a paper template (5 cm×6.4 cm) with a rectangular grid of 63 holes (2.9 mm diameter) is placed on the test specimen area below the inoculant. Using a binocular dissecting microscope with a power sufficient to magnify the diameter of a hole to one fourth of the diameter of the field of view, the test specimen is examined under each hole, assigning a 1 if there were any algae colonies of at least 60 µm in diameter, and a zero otherwise. The percentage algae infestation is calculated as the number of holes with infestation among the 63 holes. The resulting percentage of each shingle that is infested with algae over an observation period of 10 weeks is summarized in FIG. 4.

Figure 4:
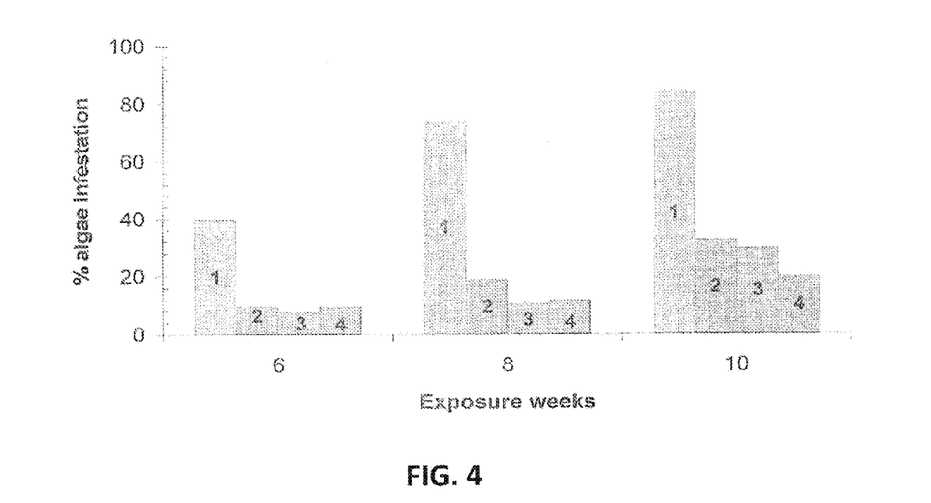
FIG. 4 includes a graph of a percentage of algae infestation observed on roofing products in accordance with an embodiment described herein.

Turning to FIG. 4, a graph of a percentage of algae infestation observed on roofing products is provided. The percentage of each of Shingles 1 through 4 that is infested with algae is reported at a period of 6 weeks, 8 weeks, and 10 weeks. Each bar in the graph is labeled with a number corresponding to the appropriate shingle. Shingle 1, without any biocidal agent incorporated, is approximately 40% infested after 6 weeks, more than 70% infested after 8 weeks, and more than 80% infested after 10 weeks. Shingle 2, with a biocidal agent conventionally incorporated, is less than 20% infested after 6 weeks, approximately 20% infested after 8 weeks, and more than 30% infested after 10 weeks. By contrast, Shingles 3 and 4, with a biocidal agent incorporated in accordance with the present invention, are less infested than Shingles 1 and 2, even after 10 weeks of exposure. In particular, Shingles 3 and 4 are less infested than Shingle 2 after 10 weeks of exposure, even though Shingle 2 includes an average weight % of copper oxide (based on the total weight % of the total amount of roofing granules on Shingle 2) that is of a similar order of magnitude as the average weight % of copper oxide (based on the total weight % of the total amount of roofing granules on either of Shingles 3 or 4) provided on the roofing granules of either Shingle 3 or 4.

Example 5

Figure 5:
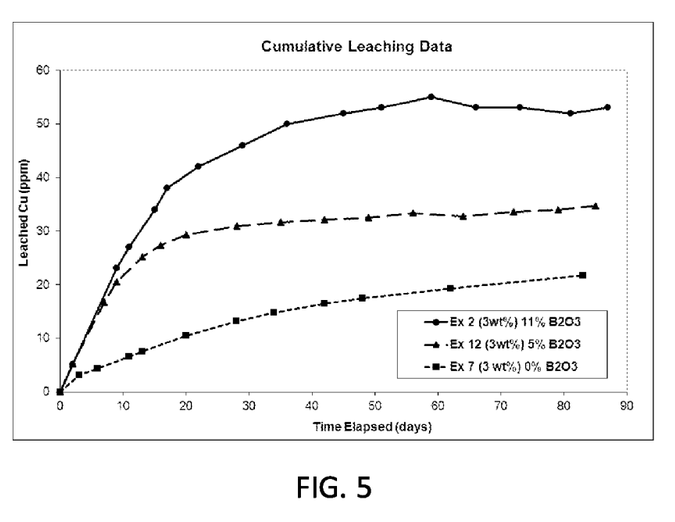
FIG. 5 includes a graph of cumulative biocidal agent ions leaching from three biocidal glass compositions over time in accordance with an embodiment described herein.

Three different samples are compared to demonstrate the influence of boron trioxide on Cu-leaching. Using an identical preparation procedure as described in Example 1 above, roofing granules are prepared using exemplary biocidal glass compositions. The leaching behavior of Ex 2 (11% $B_2O_3$), Ex 12 (5% $B_2O_3$) and Ex 7 (0% $B_2O_3$) are compared, the results illustrated in FIG. 5. Turning to FIG. 5, a graph of cumulative copper ions leached from roofing granules including the three different biocidal glass compositions is provided. The cumulative leached copper ion amount is plotted as a function of time elapsed in days.

The sample (Ex 2 with 11% $B_2O_3$) with the highest amount of boron trioxide in the glass demonstrates an initially slow rate of Cu-leaching that plateaus at the highest cumulated leached mass, i.e. the highest Cu-leaching limit value. The presence of boron trioxide within the biocidal glass composition favors the increase of the copper leachable quantity in the glass. Further, the initially slow rate of Cu-leaching is an indication of durability of the biocidal glass composition. Typically, when a glass is in contact with an aqueous solution, and in more particular, an acidic aqueous solution, the glass components diffuse into the solution as alkali ions which cause the glass to deteriorate. When a greater amount of alkali ions, such as sodium and potassium, are leached by the glass, other ions are pulled along into the aqueous solution and increase the rate the glass degrades. Hence, with the initially slow rate of Cu-leaching provided by the glass composition with the boron trioxide, less ions are leached by the glass. The presence of the boron trioxide provides a biocidal glass composition with an increased useful active lifetime compared to a biocidal glass composition without boron trioxide.

Example 6

Figure 6:
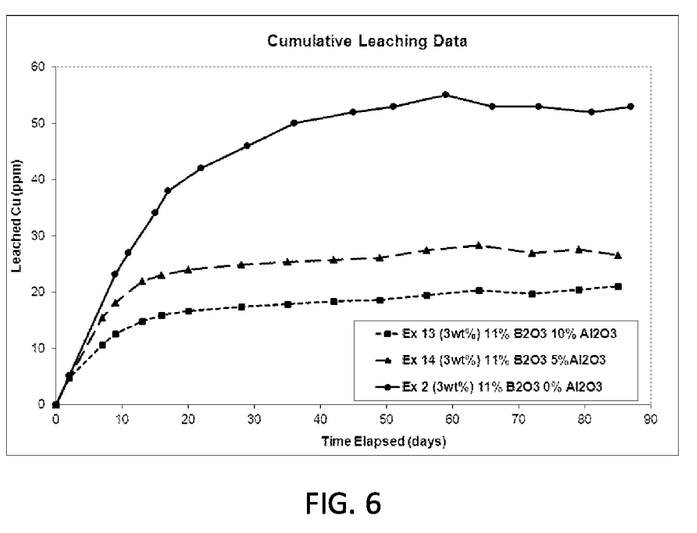
FIG. 6 includes a graph of cumulative biocidal agent ions leaching from three biocidal glass compositions over time in accordance with an embodiment described herein.

Three different samples are compared to demonstrate the influence of aluminum oxide on Cu-leaching. Using an identical formulation and preparation procedure as described in Example 1 above, roofing granules are prepared using exemplary biocidal glass compositions. The leaching behavior of Ex 13 (10% $Al_2O_3$), Ex 14 (5% $Al_2O_3$) and Ex 2 (0% $Al_2O_3$) in glasses containing 11% of boron trioxide are compared, the results illustrated in FIG. 6. Turning to FIG. 6, a graph of cumulative copper ions leached from roofing granules including the three different biocidal glass compositions is provided. The cumulative leached copper ion amount is plotted as a function of time elapsed in days. Without aluminum oxide (Ex 2), the characteristic time and Cu-leaching value are the highest. When aluminum oxide (Ex 13 and Ex 14) is added to the biocidal glass composition, both values decrease: the glass dissolution slows down in the aqueous solution at pH=5 and both Ex 13 and Ex 14 do not typically favor the Cu-leaching with relative lower Cu-leaching values compared to Ex 2. However, the presence of aluminum oxide provides the desirable properties of stability and durability for the biocidal glass composition. In particular, it has been observed that without the presence of aluminum oxide, a biocidal glass composition is degraded after a 38-day leaching test such that the glass dissolves and is no longer an effective coating on the roofing granule. The 38-day leaching test includes placing the roofing granules in the aqueous acidic solution as described above for a period of 38-days. Accordingly, in order to prevent the dissolution and degradation of the biocidal glass composition, an amount of aluminum oxide is beneficial to the stability and durability of the final biocidal glass composition.

Example 7

Figure 7:
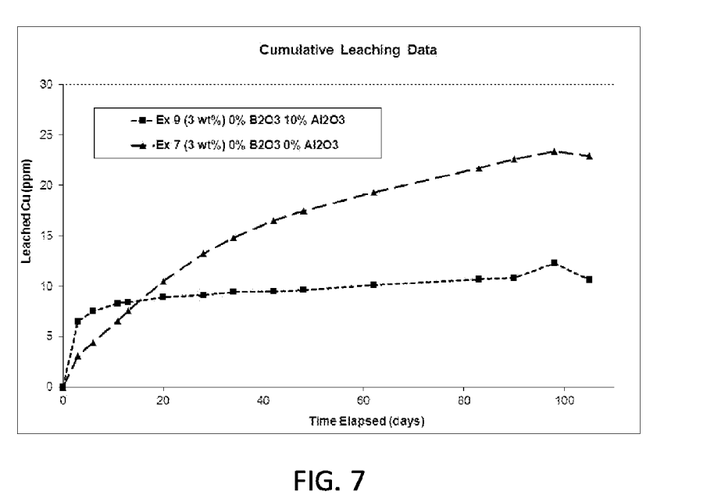
FIG. 7 includes a graph of cumulative biocidal agent ions leaching from two biocidal glass compositions over time in accordance with an embodiment described therein.

Two different samples are compared to demonstrate the influence of aluminum oxide on Cu-leaching without the presence of boron trioxide. The leaching behavior of Ex 7 (0% $Al_2O_3$) and Ex 9 (10% $Al_2O_3$) are compared, the results illustrated in FIG. 7. Turning to FIG. 7, a graph of cumulative copper ions leached from roofing granules including the two different biocidal glass compositions is provided. The cumulative leached copper ion amount is plotted as a function of time elapsed in days. As seen in FIG. 7, the presence of aluminum oxide (Ex 9) limits the Cu-leaching, i.e. decreasing the available leached Cu from the biocidal glass composition, compared to a biocidal glass composition without the aluminum oxide (Ex 7). Although the presence of aluminum oxide in the biocidal glass composition may generally decrease the available leached Cu without the presence of boron trioxide, it is advantageous to include aluminum oxide in the biocidal glass composition to provide stability and durability of the final biocidal glass composition as discussed in Example 6.

Example 8

Figure 8:
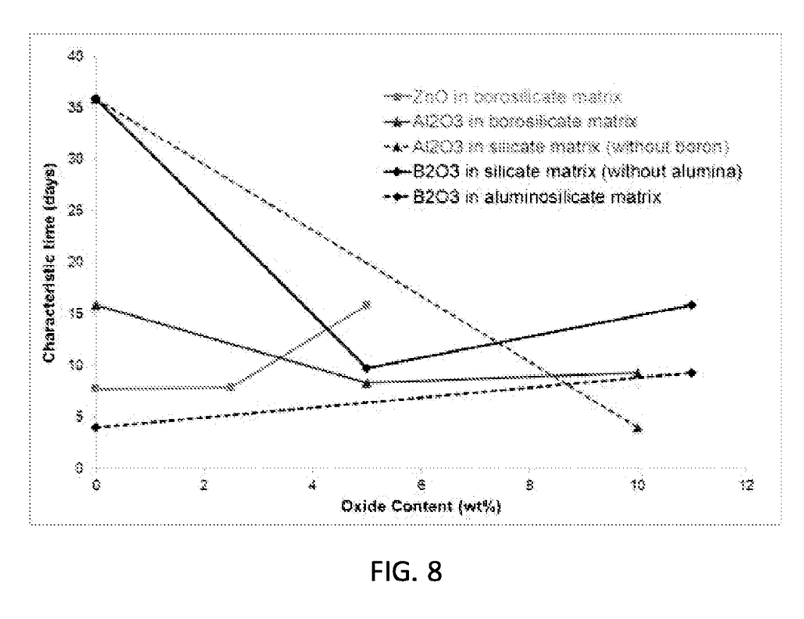
FIG. 8 includes a graph of characteristic time from several biocidal glass compositions versus oxide content in accordance with an embodiment described therein.
Figure 9:
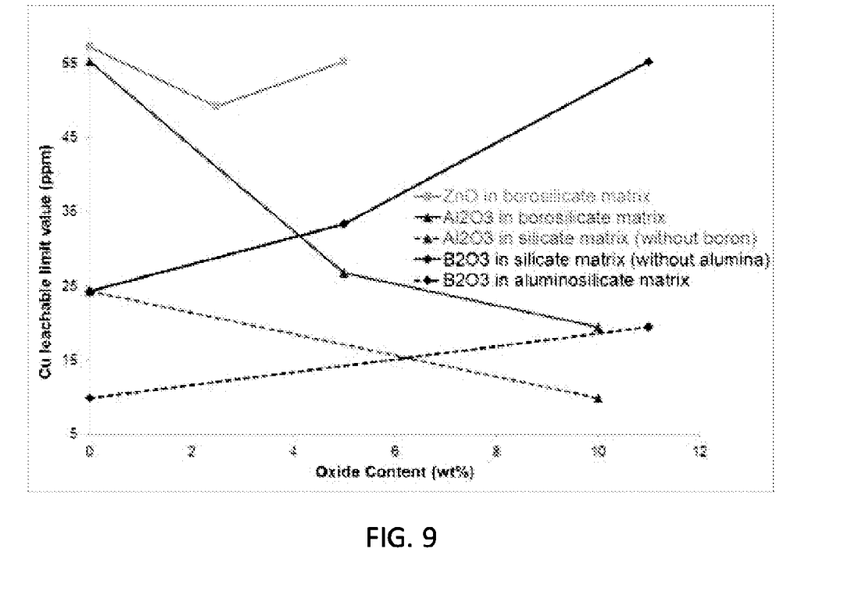
FIG. 9 includes a graph of cumulative biocidal agent ions leaching from several biocidal glass compositions versus oxide content in accordance with an embodiment described herein.

The influence of zinc oxide, aluminum oxide, boron trioxide, and combinations thereof are analyzed to demonstrate the impact of the components on the leaching of copper oxide with 3 wt % of biocidal glass on granules. FIGS. 8 and 9 are graphical illustrations of the total leached copper versus elapsed time for each varying oxide and the related characteristic times of leaching and Cu-leachable limit value. For optimal Cu-leaching, a high characteristic time and a high limit value are desired. The higher the characteristic time, the slower the release of copper (which is better for the glass durability). The higher is the limit value, the more available copper for the leaching on the granule.

As seen in FIGS. 8 and 9, the presence of boron trioxide is desired for maximum leachable Cu with a slow release. Although aluminum oxide has a generally low characteristic time, an amount of aluminum oxide may be desirable in order to stabilize the glass in the coating to avoid an increased dissolution. Further, zinc oxide clearly can be used as another biocidal agent.

Example 9

Five different samples are compared to illustrate an exemplary optimized biocidal glass composition. Simplified leaching tests are performed on the three glass powders (Ex 15, Ex 16, and Ex 17; grain size<20 μm) mixed with the clay to evaluate the reactivity of these glasses. Instead of coating the granules, a mixture of the glass with the biocidal agent (about 20 wt. % to about 44 wt. %), clay (about 17 wt. % to about 25 wt. %), water (about 7 wt. % to about 10 wt %), and sodium silicate (about 32 wt. % to about 45 wt. %) is spread on glass-ceramic plates, dried, heated up and put in an aqueous solution at pH=5 (obtained with an HCl solution). The changes of pH are recorded until the pH stabilization. The obtained pH versus time curves are plotted on FIG. 10 and compared to Ex 2 and to a coating with 20% of $Cu_2O$ (simulating the standard CT solution).

Figure 10:
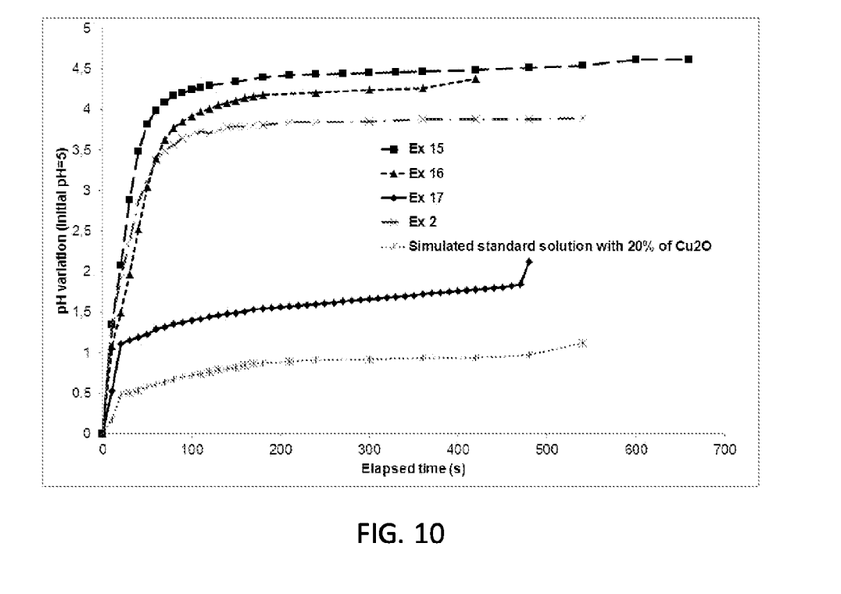
FIG. 10 includes a graph of pH variation versus time of several biocidal glass compositions in accordance with an embodiment described herein.

Looking to FIG. 10, the pH variation due to Ex 15 and Ex 16 is close to the curve of Ex 2 glass which is considered reactive with a high rate of prolonged release. The pH variation due to the Ex 17 glass is much lower—Ex 17 dissolves less in the acid solution than the other two candidates. Accordingly, with Ex 17 it is surmised that this formulation will provide improved biocidal activity as well as less needed glass quantity on the granules compared to conventional roofing granules.

Certain features, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges includes each and every value within that range.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

The specification and illustrations of the embodiments described herein are intended to provide a general demonstration of the structure of the various embodiments. The specification and illustrations are not intended to serve as an exhaustive and comprehensive description of all of the elements and features of apparatus and systems that use the structures or methods described herein. Separate embodiments may also be provided in combination in a single embodiment, and conversely, various features that are, for brevity, described in the context of a single embodiment, may also be provided separately or in any subcombination. Further, reference to values stated in ranges includes each and every value within that range. Many other embodiments may be apparent to skilled artisans only after reading this specification. Other embodiments may be used and derived from the disclosure, such that a structural substitution, logical substitution, or another change may be made without departing from the scope of the disclosure. Accordingly, the disclosure is to be regarded as illustrative rather than restrictive.

What is claimed is:

1. A coating for use with a roofing granule, the coating comprising sodium silicate, a clay, or a sol gel with a biocidal glass composition, the biocidal glass composition comprising glass doped with at least one biocidal agent, the biocidal agent at least partially solubilized within a glass composition matrix wherein the glass comprises at least one of soda-lime silicate glass, float glass, borate glass, or combinations thereof, the at least one biocidal agent comprising about 0.01 wt. % to about 50 wt. % of a total weight % of the biocidal glass composition, wherein the at least one biocidal agent comprises copper oxide present at about 20 wt. % to about 50 wt. % of the total weight of the biocidal glass composition, the biocidal glass composition having a solubility when exposed to an aqueous environment and the at least one biocidal agent has a first steady normalized flux from the biocidal glass composition after about 2 to about 4 years under normal outdoor weather conditions, wherein the roofing granule has an L* value of at least 40 as measured by a CIE LAB color scale.

2. A roofing granule comprising:
a base particle; and
a coating formed on a surface of the base particle, wherein the coating comprises sodium silicate, a clay, or a sol gel with a biocidal glass composition comprising glass doped with at least one biocidal agent, the biocidal agent at least partially solubilized within a glass composition matrix wherein the glass comprises at least one of soda-lime silicate glass, float glass, borate glass, or combinations thereof, and wherein the at least one biocidal agent comprises about 0.01 wt. % to about 50 wt. % of a total weight % of the biocidal glass composition, wherein the at least one biocidal agent comprises copper oxide present at 20 wt. % to about 50 wt. % of the total weight of the biocidal glass composition, the biocidal glass composition having a solubility when exposed to an aqueous environment and the at least one biocidal agent has a first steady normalized flux from the biocidal glass composition after about 2 to about 4 years under normal outdoor weather conditions, wherein the roofing granule has an L* value of at least 40 as measured by a CIE LAB color scale.

3. A process of forming a roofing granule comprising:
providing a base particle; and
forming a coating on a surface of the base particle, wherein the coating comprises sodium silicate, a clay, or a sol gel with a biocidal glass composition, wherein the biocidal glass composition comprises a glass doped with at least one biocidal agent, the biocidal agent at least partially solubilized within a glass composition matrix wherein the glass comprises at least one of soda-lime silicate glass, float glass, borate glass, or combinations thereof, and wherein the at least one biocidal agent comprises about 0.01 wt. % to about 50 wt. % of a total weight % of the biocidal glass composition, wherein the at least one biocidal agent comprises copper oxide present at 20 wt. % to about 50 wt. % of the total weight of the biocidal glass composition, the biocidal glass composition having a solubility when exposed to an aqueous environment and the at least one biocidal agent has a first steady normalized flux from the biocidal glass composition after about 2 to about 4 years under normal outdoor weather conditions, wherein the roofing granule has an L* value of at least 40 as measured by a CIE LAB color scale.

4. The coating of claim 1, wherein the at least one biocidal agent further comprises at least one of zinc oxide, silver oxide, tin oxide, or combinations thereof.

5. The coating of claim 1, wherein the glass comprises silicon dioxide in an amount of about 20 wt. % to about 60 wt. %, boron trioxide in an amount of about 0.1 wt. % to about 20.0 wt. %, and aluminum oxide in an amount of about 0.01 wt. % to about 12.0 wt. %, based on the total weight % of the biocidal glass composition.

6. The coating of claim 5, wherein the glass further comprises at least one of calcium oxide, magnesium oxide, sodium oxide, potassium oxide, or combinations thereof.

7. The coating of claim 1, wherein the biocidal glass composition comprises a powder comprising a plurality of particles.

8. The coating of claim 7, wherein the plurality of particles comprise an average grain size distribution of less than about 100 μm.

9. The coating of claim 1, wherein the biocidal glass composition comprises about 0.1 wt. % to about 30 wt. % of a total weight % of the roofing granule.

10. The coating of claim 1, wherein the glass is doped with a second biocidal agent, wherein the second biocidal agent has a second steady normalized flux from the biocidal glass composition different from the first steady normalized flux after about 2 to about 4 years under normal outdoor weather conditions.

11. The coating of claim 1, wherein the roofing granule is part of a total amount of roofing granules on a roofing product and wherein the roofing granule comprises up to about 100% of the total amount, up to about 50% of the total amount, or within a range of about 0.5% to about 30% of the total amount of roofing granules on the roofing product.

12. The coating of claim 11, wherein the at least one biocidal agent comprises at least 0.1 wt. % of a total weight % of the total amount of granules on the roofing product.

13. The coating of claim 11, wherein the roofing product comprises an asphalt-based shingle.

14. The coating of claim 1, wherein at least a portion of the at least one biocidal agent is encapsulated in the glass.

15. The roofing granule of claim 2, wherein the coating has an average thickness of between about 2 μm to about 200 μm.

* * * * *